United States Patent [19]

Falk

[11] 4,420,434
[45] Dec. 13, 1983

[54] PERFLUORALKYL ANION/PERFLUOROALKYL CATION ION PAIR COMPLEXES

[75] Inventor: Robert A. Falk, New City, N.Y.

[73] Assignee: Ciba-Geigy Corporation, Ardsley, N.Y.

[21] Appl. No.: 223,640

[22] Filed: Jan. 9, 1981

[51] Int. Cl.$^3$ .................... C07C 143/00; C07C 53/00
[52] U.S. Cl. .................... 260/501.12; 260/501.15; 260/501.16; 260/501.21; 260/963; 546/346; 546/246; 546/247; 546/248; 546/340; 546/344; 546/338; 544/158; 544/159; 544/161; 544/168; 544/170; 544/175; 544/398; 544/399; 544/400; 544/401; 252/3; 252/2
[58] Field of Search .................... 260/501.12, 501.15, 260/501.16, 501.21, 963; 546/346, 246, 247, 248, 340, 344, 338; 544/158, 159, 161, 168, 170, 175, 398, 399, 400, 401

[56] References Cited

U.S. PATENT DOCUMENTS

| | | | |
|---|---|---|---|
| 2,691,043 | 10/1954 | Husted et al. | 260/501.16 |
| 2,727,923 | 12/1955 | Husted | 260/501.15 |
| 3,839,343 | 10/1974 | Anello et al. | |
| 4,168,277 | 9/1979 | Witsdake et al. | 260/501.15 |

FOREIGN PATENT DOCUMENTS 55-3428   1/1980   Japan.
55-45459  3/1980   Japan.

*Primary Examiner*—Bernard Helfin
*Attorney, Agent, or Firm*—Michael W. Glynn

[57] ABSTRACT

The instant invention relates to the use of ion-pair complexes derived from anionic perfluoroalkyl sulfonates, carboxylates, phosphates and phosphonates and cationic perfluoroalkyl surfactants. Such complexes are capable of reducing the surface tension of aqueous solutions dramatically even at extremely low concentrations, and are useful as wetting, spreading and leveling agents and are especially preferred as components in so-called aqueous film forming foam compositions for fighting polar and non-polar solvent and fuel fires.

4 Claims, No Drawings

PERFLUORALKYL ANION/PERFLUOROALKYL CATION ION PAIR COMPLEXES

BACKGROUND OF THE INVENTION

It is well known that conventional hydrocarbon surfactants can lower the surface tension of aqueous solutions to as low as 23 dynes/cm, while fluorinated surfactants can attain surface tensions in the 15 to 20 dynes/cm range. While fluorinated surfactants have proven to be much more efficient as surface tension depressants than hydrocarbon surfactants, their use has has been severely limited because of their high cost. The problem of attaining lowest possible surface tension with the smallest possible amount of highly priced fluorinated surfactants or surfactant/synergist systems has been the subject of many patents and publications. It is an object of the present invention to provide novel perfluoralkyl or $R_fR_f$ ion pair complexes which are capable of reducing the surface tension of aqueous systems to levels which are below the surface tensions achieved with equal amounts of the individual anionic and cationic perfluoroalkyl surfactants from which the novel $R_fR_f$ ion-pair complexes are derived.

Four general classes of surfactants are commonly represented as useful surface tension depressants, namely cationic, anionic, amphoteric and nonionic surfactants. In many applications, combinations of hydrocarbon surfactants are used in order to achieve certain results. It is generally known that nonionic and amphoteric surfactants can be used in combination with each other as well as in combination with either anioic surfactants or cationic surfactants. Such surfactant mixtures are said to be compatible. It is also generally known that anionic and cationic surfactants should not be used in combination with each other, because they are incompatible. The reason combinations of anionic and cationic are called incompatible is that they react with each other and form poorly soluble hydrocarbon-hydrocarbon complexes plus salts, as described in Kirk-Othmer, Encyclopedia of Chemical Technology, 19, 555, 2nd Ed., (1966) and Milton J. Rosen, Surfactants and Interfacial Phenomena, J. Wiley, 24.

These hydrocarbon cation/hydrocarbon anion complexes are simply referred to as $R_hR_h$ complexes and have been described by Hummel as electroneutral substances. See Hummel, D., *Identification and Analysis of Surface-Active Agents*, Interscience, New York 1962 (p. 23). It has been reported that certain mixtures of hydrocarbon type anionic and cationic surfactants in some cases can exhibit low surface tensions. Corkill, see J. M. Corkill et al., Proc. Roy. Soc. (London) Series A273 (1963), was the first to show that mixtures of sodium decyl sulfate and decyltrimethylammonium bromide or the ion-pair hydrocarbon salt decyltrimethylammonium decyl sulfate give virtually identical surface tension-concentration curves and surface tension values as low as 22 dynes/cm.

Mannheimer (U.S. Pat. No. 3,661,945) showed that select structural types of anionics and cationics could give useful reaction products.

L. G. Anello and R. F. Sweeney (U.S. Pat. No. 3,839,343) has reported the preparation of a symmetrical polyfluoroisoalkoxyalkyl quaternary ammonium sulfates—$[(CF_3)_2CFO(CF_2)_3(CH_2)_tNR_x]^\oplus O^\ominus SO_2O(CH_2)_t(CF_2)_3OCF(CF_3)_2$.

It has now been surprisingly found that $R_fR_f$ ion-pair complexes made by reacting equimolar amounts of specific classes of anionic and cationic $R_f$-surfactants are extremely useful and efficient surface tension depressants even though such $R_fR_f$ complexes have been found to be very much less soluble than the anionic and cationic surfactants from which they were derived, and are in most cases practically insoluble in water (solubility of less than 0.001% by weight).

Most importantly, it was found that stable dispersions of the waterinsoluble $R_fR_f$ ion-pair complexes can be made and, quite significantly, it was found that such $R_fR_f$ ion-pair complex dispersions provide considerably lower surface tension properties in water at extremely low concentrations than did equal amounts of either the anionic or cationic fluorochemical surfactants from which the $R_fR_f$ ion-pair complex was derived.

Furthermore, it was found that the novel $R_fR_f$ ion-pair complexes are most useful as additives to so-called AFFF agents or aqueous film forming foams. These so-called AFFF agents act in two ways:

(a) As aqueous foams they are used as primary fire extinguishing agents, and (b) As vapor sealants they prevent the reignition of fuels and solvents. It is this second property which makes AFFF agents far superior to other known fire fighting agents for fighting fuel and solvent fires. This vapor sealing action of an AFFF agent is achieved by the spreading of the aqueous AFFF agent solution over the fuel surface.

The criterion necessary to attain spontaneous spreading of two immiscible phases has been taught by Harkins et al., J. Am. Chem. 44, 2665 (1922). The measure of the tendency for spontaneous spreading is defined by the spreading coefficient (SC) as follows:

$$SC = \delta a - \delta b - \delta i$$

where
SC = spreading coefficient
$\delta a$ = surface tension of the lower liquid phase
$\delta b$ = surface tension of the upper aqueous phase
$\delta i$ = interfacial tension between the aqueous upper phase and lower liquid phase If the SC is positive, the solution should spread and film formation should occur. The greater the SC, the greater the spreading tendency. This requires the lowest possible aqueous surface tension and lowest interfacial tension.

Based on the Harkins equation it is obvious that the most efficient surface tension depressants and interfacial tension depressants will yield aqueous film forming foams with the highest spreading coefficient.

Aqueous solutions with very low surface tensions used for the extinguishment of hydrocarbon fuel fires were first disclosed by N. O. Brace in U.S. Pat. No. 3,047,619 and 3,091,614. Brace utilized sprays of aqueous solutions containing $R_f$ surfactants of the beta-hydroperfluoroalkyl type. Similarly, Tuve, et al., disclosed the use of aqueous solutions containing $R_f$-surfactants derived from perfluorinated acids of the $R_fCOOH$ and $R_fSO_3H$ type as fire fighting foams in U.S. Pat. No. 3,258,423.

While $R_f$-surfactants reduce the surface tension of aqueous solutions to as low as 15 dynes/cm, they generally do not reduce interfacial tension properties to the same degree as many hydrocarbon surfactants.

Aqueous solutions containing $R_f$-surfactants and hydrocarbon surfactants having very low surface tensions as well as low interfacial tension properties, and therefore a positive spreading coefficient when measured against hydrocarbon solvents, were prepared by Klevens and Raison, J. Chim. Phys., 51, p. 1–8 (1959). The 3M Company, a manufacturer of $R_f$-surfactants, recommended in their technical bulletins (3M Brand Fluorochemical Surfactants, June 15, 1963, pp. 1–45) the combination of $R_f$-surfactants and hydrocarbon surfactants to achieve low surface tension and low interfacial tension in aqueous solutions and therefore a positive spreading coefficient.

Solutions of fluorochemical surfactants and hydrocarbon surfactants were used the first time by Ratzer as fire fighting foams and disclosed at the "Fourth Quinquennial Symposium on Fire Fighting Foam", Aug. 11/12/13, 1964 at Campobello, and published in the minutes of the above symposium, and in "Foam" October 1964, No. 24 (a publication of the Mearl Corporation, Ossining, N.Y.). Drs. Shinoda and Fujihira reported the use of mixtures of fluorochemical and hydrocarbon surfactants in the context of various commercial applications including fire extinguishing agents at a Meeting on the Research on Oil sponsored by the Japan Oil Chemists' Society and the Chemical Society of Japan Chemistry on Nov. 2-3, 1966 at Nagoya, Japan. Fire fighting agents based on aqueous solutions containing fluorochemical surfactants and hydrocarbon surfactants, as disclosed the first time by Ratzer are today commonly known as AFFF agent or Aqueous Film Forming Foams. Many U.S. Pat. Nos. disclosing AFFF agent compositions based on fluorochemical surfactants and hydrocarbon surfactants have since issued, such as 3,047,619; 3,257,407; 3,258,423; 3,562,156; 3,621,059; 3,655,555; 3,661,776; 3,677,347; 3,759,981; 3,772,195; 3,798,265; 3,828,085; 3,839,425; 3,849,315; 3,941,705; 3,952,075; 3,957,657; 3,957,658; 3,963,776; 4,038,195; 4,042,522; 4,049,556; 4,060,132; 4,060,489; 4,069,158; 4,090,967; 4,099,574; 4,149,599; 4,203,850; 4,209,407.

In U.S. Pat. No. 4,089,804, R. A. Falk discloses a method to improve $R_f$-surfactants by employing water-insoluble $R_f$-synergists, and in U.S. Pat. No. 4,090,967, AFFF agents are disclosed by Falk which contain $R_f$-surfactants, $R_f$-synergists and hydrocarbon surfactants among other ingredients. With the help of water insoluble $R_f$-synergists it has now become not only possible to reduce the content of the costly $R_f$-surfactants in an AFFF agent by up to 50% (and still meet U.S. military specifications for AFFF agents), but it also became possible to improve and utilize certain $R_f$-surfactants in AFFF agent compositions which in the absence of the novel water-insoluble $R_f$-synergists would not provide aqueous solutions with positive spreading coefficients.

However, a deficiency in prior-art AFFF agents continues to be (a) the amount of high priced fluorochemical required to achieve the proper performance, which limits the use of AFFF agents and (b) the inherent fish toxicity due to the high surfactant content in AFFF agents.

Since the AFFF agents ultimately enter the aquatic ecosystem, it has been customary to choose at least one or two aquatic species to assess potential aquatic toxicity and extrapolate generally two other species. The U.S. Navy screens AFFF agents toxicity on the Mummichog (fundulus heteroclitus) in artificial sea water. Agents are compared by 96 hour active exposure tests to determine the concentration lethal to 50% of the organisms; this is the 96 hour median lethal concentration or $LC_{50}$.

It has now been found that the novel $R_fR_f'$ ion-pair complexes are partial or complete substitutes for the fluorochemical surfactants used in prior-art AFFF agents which will (a) reduce cost due to the use of smaller amounts of the more efficient ion-pair complexes, (b) will increase the efficiency of the AFFF agents and (c) reduce the fish toxicity significantly.

DETAILED DISCLOSURE

The instant invention relates to hydrolytically stable $R_fR_f'$ ion-pair complexes having the formula:

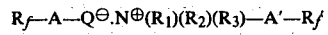

wherein $R_f$ and $R_f'$ independently represent straight or branched chain perfluoroalkyl of 4 to 18 carbons;

A and A' independently represent a divalent covalent linking group of unrestricted structure, but is typically a straight or branched substituted or unsubstituted aliphatic chain of 1 to 18 atoms and may include either, sulfide, sulfone, sulfoxide, trivalent nitrogen atoms bonded only to carbon atoms, carbonyl, sulfonamido, carbonamido, arylene groups and the like, with the proviso that A may be a direct bond, but A' must contain at least 1 carbon atom;

Q represents carboxylate, sulfonate, phosphate and phosphonate.

$R_1$, $R_2$ and $R_3$ are independently hydrogen, phenyl, or alkyl of 1 to 8 carbon atoms which are unsubstituted or substituted by halo, hydroxy or aryl, $-(CHR_4CH_2O)_yR_5$ where y is 1 to 20, $R_4$ is hydrogen or alkyl of 1 to 4 carbon atoms, $R_5$ is hydrogen or methyl, or $R_1$ and $R_2$ taken together with the nitrogen to which they are attached represent piperidino, morpholino, or piperazino; or wherein $R_1$, $R_2$ and $R_3$ taken together with the nitrogen to which they are attached represent pyridinium, or substituted pyridinium

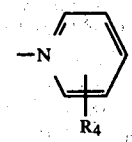

A preferred class of complexes are those of the above formula wherein $R_f$ is perfluoroalkyl of 4 to 12 carbon atoms;

A and A' independently represent a divalent covalent linking group of the formula

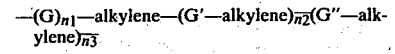

wherein

G, G' and G" independently represent —O—, —S—, —SO$_2$—, —SO$_2$NH—,

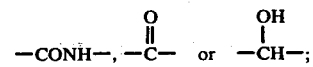

$n_1$ is 0 or 1;

$n_2$ and $n_3$ are independently 0, 1 or 2;

alkylene is straight or branched chain alkylene of 1 to 8 carbon atoms, with the proviso that each aliphatic chain A and A' contains no more than 18 carbon atoms and the $R_f$ and $R_f'$ group, respectively, is bonded to the left hand side of said covalent linking group,
and A additionally represents a direct bond;
$R_1$, $R_2$ and $R_3$ are lower alkyl; and
Q is carboxylate, sulfonate, phosphate or phosphonate.
Highly preferred are those within said preferred class wherein $R_f$ is perfluoroalkyl of 4 to 12 carbon atoms;
A and A' independently represent
—CH$_2$CH$_2$—S—alkylene—G'—alkylene— wherein G' is —SO$_2$NH— or

and each alkylene is straight or branched chain of from 1 to 6 carbon atoms;
$R_1$, $R_2$ and $R_3$ are methyl; and
Q is carboxylate, sulfonate, phosphate or phosphonate.
Most highly preferred are those complexes wherein Q is sulfonate, carboxylate or phosphate.

The instant $R_fR_f'$ ion-pair complexes are derived from anionic and cationic fluorochemical surfactants according to the following equation:

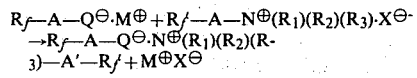

wherein $R_f$, $R_f'$, A, A', Q, $R_1$, $R_2$ and $R_3$ are previously described and M is an aqueous solvatable cation such as hydrogen, alkali or alkaline earth metal cation, tetramethyl ammonium or other simple quaternary ammonium cation and X is an aqueous solvatable anion such as chloride, bromide, iodide, methyl sulfate and the like.

The synthesis of the $R_fR_f'$ ion-pair complexes can be carried out in several ways.

One method consists of reacting equimolar amounts of concentrated aqueous solutions of the respective anionic and cationic $R_f$ surfactants. These complexes will precipitate from the concentrated solutions and can be filtered, washed and dried. This method yields the complexes in solid form, substantially free from (a) trace amounts of unreacted surfactants, surfactant precursors and (b) free from salts formed during the reaction.

A second method consists of reacting equimolar amounts of the respective surfactants in a solvent-water mixture. It was found that in a preferred solvent-water mixture high solid content dispersions of the novel complexes can be obtained which have shown to possess good stability. This method of synthesis is a preferred method if removal of (a) trace amounts of unreacted surfactants and surfactant precursors and (b) removal of the salt formed during the reaction is not necessary. It was found that such high solid content dispersions will precipitate if diluted with water. However, it was also found that blending such high solid content complex dispersions with micelle forming surfactants prior to dilution with water can prevent such precipitation. Similarly, dilution of high solid content dispersions with selected solvents or solvent-water mixtures can prevent precipitation of the water-insoluble complexes.

A third synthesis involves the reaction of anionic and cationic surfactant solutions in which either the anionic or the cationic surfactant is present in a higher than equimolar amount. As a result a mixture of a $R_fR_f'$ ion-pair complex and an anionic or cationic surfactant will be formed, which will have increased stability even if diluted to lower concentrations with water. Instead of carrying out the above described reaction with an excess amount of either the anionic or cationic surfactant, it is also possible to carry out the reaction with equimolar amounts of anionic and cationic surfactant in the presence of sufficient amounts of a micelle forming nonionic or amphoteric surfactant in order to prevent precipitation of high solid content dispersions upon dilution with water.

A fourth method, ideal for laboratory purposes, yielding very pure complexes is based on the reaction of anionic and cationic surfactants in a dialysis cell. By selecting the proper dialysis membranes, unreacted surfactant, precursors and salts formed during the complex formation as well as solvents will diffuse through the membrane, leaving analytically pure complexes as precipitates or solutions in the dialysis cell.

The individual anionic and cationic fluorochemical surfactants which are used to make the $R_fR_f'$ ion-pair complexes are known compounds, per se, and a number of useful anionic and cationic fluorochemical surfactants are sold commercially by the following companies under the following trade names:

Asahi glass (Surflon S-); Bayer (FT-Typen); CIBA-GEIGY (LODYNE); Dainippon Inc. (Magafac); Du-Pont (Zonyl); Hoechst (Licowet, Fluorwet); I.C.I. (Monflor); Neos (Ftergent); Tohaku Hiryo (F-Top); Ugine-Kuhlman (Forofac); 3M (Fluorad).

Illustrative examples of anionic and cationic fluorochemical surfactants used for the synthesis of the instant $R_fR_f'$ ion-pair complexes are disclosed in the following patents and are herein incorporated by reference in toto:

U.S. Pat. Nos. 2,727,923; 2,759,019; 2,764,602; 2,764,603; 3,147,065; 3,147,066; 3,207,730; 3,257,407; 3,350,218; 3,510,494; 3,681,441; 3,759,981; 3,836,552; 3,933,819; 4,014,926; 4,062,849 and 4,098,811;

German Offen. Nos. 2,013,104; 2,224,653; 2,357,916; 2,732,555; 1,925,555; 2,127,232; 2,230,366; 2,236,729; 2,337,638 and 2,523,402;

French Pat. Nos. 2,035,589; 2,241,542 and 2,333,564;
Belgium Pat. Nos. 788,335 and 801,585;
British Pat. Nos. 1,270,622; 1,288,678 and 1,435,200.

Other illustrative examples of $R_f$-surfactants which can be used for the synthesis of the $R_fR_f'$ ion-pair complexes are the below shown acids and their alkali metal salts. Preferred anionic groups are carboxylate, phosphate and sulfonate. The anionic surfactant may be used as free acid, an alkali metal salt thereof, ammonium or substituted ammonium. The patent numbers appearing in parenthesis are patents which more fully disclose the represented clss of compounds. The disclosures of these patents are incorporated herein by reference.

| Carboxylic Acids and Salts Thereof | |
|---|---|
| $R_fCOOH$ | (Scholberg el at., J. Phys. Chem. 57,923-5 (1953) |
| $R_f(CH_2)_{1-20}COOH$ | (Ger. 1,916,669) |
| $R_fO(CH_2)_{1-20}COOH$ | (U.S. Pat. No. 3,409,647) |
| $R_fSO_2N(C_2H_5)CH_2COOH$ | (U.S. Pat. No. 3,258,423) |
| $(C_2F_5)_2(CF_3)CCH_2COOH$ | (Brit. 1,176,493) |
| $C_{10}F_{19}OC_6H_4CON(CH_3)CH_2COOH$ | (Brit. 1,270,662) |
| $R_f(CH_2)_{1-3}SCH(COOH)CH_2COOH$ | (U.S. Pat. No. 3,706,787) |
| $R_f(CH_2)_{1-12}S(CH_2)_{1-17}COOH$ | (Ger. 2,239,709; U.S. Pat. No. 3,172,910) |
| Sulfonic Acids and Salts Thereof | |
| $R_fSO_3H$ | (U.S. Pat. No. 3,475,333) |
| $R_fC_6H_4SO_3H$ | (Ger. 2,134,973) |

-continued

| | |
|---|---|
| $R_f(CH_2)_{1-20}SO_3H$ | (Ger. 2,309,365) |
| $R_fSO_2NHCH_2C_6H_4SO_3H$ | (Ger. 2,315,326) |
| $R_fSO_2N(CH_3)(C_2H_4O)_{1-20}SO_3H$ | (S.A. 693,583) |
| $R_fCH_2CH_2OCH_2CH_2CH_2SO_3H$ | (Can. 842,252) |
| $R_fOC_6H_4SO_3H$ | (Ger. 2,230,366) |
| $C_{12}F_{23}OC_6H_4SO_3H$ | (Ger. 2,240,263) |
| $(C_2F_5)_3CO(CH_2)_3SO_3H$ | (Brit. 1,153,854) |
| $CF_3(C_2F_5)_2CO(CH_2)_3SO_3H$ | (Brit. 1,153,854) |
| $(C_2F_5)_2(CF_3)CCH=C(CF_3)SO_3H$ | (Brit. 1,206,596) |
| $R_f(CH_2)_1$ or $_2O-(C_2H_4O)_{1-12}-SO_3H$ | (Ger. 2,310,426) |
| Phosphonates, Phosphates, Related Phosphoro Derivatives | |
| $R_fPO(OH)_2$ | (Ger. 2,110,767) |
| $R_fSO_2N(Et)C_2H_4OPO(OH)_2$ | (Ger. 2,125,836) |
| $R_fCH_2OPO(OH)_2$ | (Ger. 2,158,661) |
| $C_8F_{15}OC_6H_4CH_2PO(OH)_2$ | (Ger. 2,215,387) |
| $R_fOC_6H_4CH_2PO(OH)_2$ | (Ger. 2,230,366) |

The commercially available surfactants used in the following examples are:

FC-95, which is an alkali metal salt of perfluoroalkyl-sulfonic acid; CAS Registry No. 2795-39-3; $C_8HF_{17}O_3S.K$.

FC-128, which is a perfluoroalkanesulfonamido alkylenemonocarboxylic acid salt as disclosed in U.S. Pat. No. 2,809,990; $C_{12}H_8F_{17}NO_4S.K$; CAS Registry No. 2991-51-7.

FC-134, which is a cationic quaternary ammonium salt derived from a perfluoroalkanesulfonamidoalkylenedialkylamine as disclosed in U.S. Pat. No. 2,759,019; $C_{14}H_{16}F_{17}N_2O_2S.I$; CAS Registry No. 1652-63-7.

Zonyl FSC, a cationic quaternary ammonium salt derived from linear perfluoroalkyl telomers.

Zonyl FSA and FSP, anionics derived from linear perfluoroalkyl telomers.

Monflor 31 and 32, anionics derived from branched tetrafluoroethylene oligomers as disclosed in GB Pat. No. 1,148,486.

Monflor 72, a cationic derived from branched tetrafluoroethylene oligomers as disclosed in DT Pat. No. 2,224,653.

The following Table 1 illustrates how a selected type of an $R_fR_f$ ion-pair complex differs in its properties from the precursor anionic and cationic fluorochemical surfactants. Besides the differences shown in Table 1 (solubility, melting point, surface tension), $R_fR_f$ ion-pair complexes also differ in many other properties from their precursor surfactants.

The instant $R_fR_f$ ion-pair complexes, preferably in the form of aqueous dispersions, are very efficient surface tension suppressants and are useful in many applications where improved wetting, spreading and leveling is required. Because $R_fR_f$ ion-pair complexes are neutral species, they are compatible with nonionic, amphoteric, anionic and cationic surfactants, be they of the hydrocarbon or fluorocarbon type, as well as fluorochemical synergists as described in U.S. Pat. No. 4,089,804. It was also found that the instant $R_fR_f$ ion pair complexes do impart oil and water repellency to substrates such as textiles, fibers, nonwovens and paper. However, the preferred utility of the novel $R_fR_f$ ion-pair complexes is in the field of aqueous film forming foams ro so-called AFFF agents used in fighting polar and non-polar solvent and fuel fires. As will be shown in the experimental part, $R_fR_f$ ion-pair complexes can be successfully used as additives to AFFF agent compositions as disclosed in, but not limited to, U.S. Pat. Nos.: 3,047,619; 3,257,407; 3,258,423; 3,562,156; 3,621,059; 3,655,555; 3,661,776; 3,677,347; 3,759,981; 3,772,195; 3,798,265; 3,828,085; 3,839,425; 3,849,315; 3,941,705; 3,952,075; 3,957,657; 3,957,658; 3,963,776; 4,038,195; 4,042,522; 4,049,556; 4,060,132; 4,060,489; 4,069,158; 4,090,967; 4,099,574; 4,149,599; 4,203,850; 4,209,407.

As additives to prior-art AFFF agents the novel $R_fR_f$ ion-pair complexes will generally increase the spreading coefficient and therefore fire fighting performance and will reduce, in addition, fish toxicity of the AFFF agent. Rather than using the $R_fR_f$ ion-pair complexes as additional additives to prior art AFFF agent compositions it is recommended to use the ion-pair complexes as partial or complete substitutes for the fluorochemical surfactants present in the prior-art AFFF agent. Since it is possible to substitute larger quantities of fluorochemical surfactants with smaller quantities of the highly efficient $R_fR_f$ ion-pair complexes, it is possible to reduce the cost of the AFFF agent without reducing performance.

Commercial AFFF agents are primarily used today in so-called 6%, 3% and 1% proportioning systems. This means that 6, 3 or 1 part of an AFFF agent concentrate are diluted (proportioned) with 94, 97 or 99 parts of water (fresh, sea or brackish water) and applied by conventional foam making equipment. Preferred AFFF agent concentrates based on the novel $R_fR_f$ ion-pair complexes useful for 6, 3 and 1% proportioning comprise the following components, numbered D through M:

D. 0.05 to 5% by weight of an $R_fR_f$ ion-pair complex of the type $R_f$-A-$Q^\ominus.N^\oplus(R_1)(R_2)(R_3)$-A'-$R_f'$ and

TABLE 1

Physical Properties of $R_fR_f$ Complexes and The Surfactants From Which They are Prepared

| Physical Properties | Anionic $R_f$—Surfactant[1] | Cationic $R_f$—Surfactant[2] | $R_fR_f$—Complex[3] |
|---|---|---|---|
| Melting Point ° C. | ~208–211 | Too hygroscopic to determine | ~148–155 |
| Solubility in water % by wt. | >1 | >1 | ≈0.001 |
| Surface tensions in Deionized water (dynes/cm | | | |
| Concentration 0.001% by wt. | 42.0 | 41.7 | 26.9 |
| 0.01% by wt. | 24.5 | 24.4 | 16.1[4] |

[1] $R_fCH_2CH_2SCH_2CH_2CONHC(CH_3)_2CH_2SO_3^\ominus Na^\oplus$
[2] $R_fCH_2CH_2SCH_2CH(OH)CH_2N^\oplus(CH_3)_3Cl^\ominus$
[3] $R_fCH_2CH_2SCH_2CH_2CONHC(CH_3)_2CH_2SO_3^\ominus N^\oplus(CH_3)_3CH_2CH(OH)CH_2SCH_2CH_2R_f'$
$R_f = C_6F_{13}$ and $C_8F_{17}$ (1:1 by wt.)
[4] Aqueous solution with 0.01% by wt. of $R_fR_f$ complex is supersaturated and will form a precipitate after standing for several hours Such other properties include foaming (Ross-Miles Test), wetting (Draves-Clarkson Test), CMC (Critical Micelle Concentration), ionization constants, etc.

E. 0 to 25% by weight of nonionic, amphoteric, anionic or cationic fluorochemical surfactants
F. 0 to 55 of a fluorochemical synergist
G. 0 to 40% by weight of a hydrocarbon surfactant
H. 0 to 70% by weight of a water miscible solvent;
I. 0 to 5% by weight of an electrolyte;
K. 0 to 10% by weight of a polymeric foam stabilizer;
L. 0 to 10% by weight of a polysaccharide, and
M. Water in the amount to make up the balance of 100%.

A preferred $R_f \cdot R_f$ complex (Compound D) is represented by the formula:

$$R_f R_{11}-SCH_2CHCNHC-C-SO_3^\ominus \cdot NR_1R_2R_3CH_2CHCH_2S-R_{11}-R_f$$

(with substituents $R_6$, $R_7$, $R_8$, $R_9$, $R_{10}$, and OH)

where $R_6$ is hydrogen or lower alkyl; each of $R_7$, $R_9$ and $R_{10}$ is individually hydrogen or alkyl group of 1–12 carbons; $R_8$ is hydrogen, alkyl of 1 to 12 carbons, phenyl, tolyl, and pyridyl; and $R_{11}$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom is secondary or tertiary.

Preferred fluorochemical surfactants (Component E) are broadly chosen from among anionic, nonionic, amphoteric or cationic $R_f$ surfactants as cited in U.S. Pat. No. 4,090,967, incorporated herein by reference and in pending application U.S. Ser. No. 129,872 (Mar. 13, 1980).

Preferred are:

$$\left[ R_f R_{11}-SCH_2CH-CNHC-C-SO_3 \right]_n M$$

(with substituents $R_6$, $R_7$, $R_8$, $R_9$, $R_{10}$)

as noted in U.S. Pat No. 4,090,967, and the foam stabilizing oligomeric surfactants of formula $R_f\text{-}E\text{-}S\text{-}[M_1]_x[M_2]_y H$ and mixtures thereof which may be incorporated to improve burnback resistance and resistance to fuel penetration. These oligomers as well as their preparation are more fully described in assignee's copending application Ser. No. 129,872 filed Mar. 13, 1980 by E. Kleiner, T. Cooke and R. Falk, the disclosure of which is incorporated herein.

Preferred is an oligomer wherein $R_f$ is a straight chain perfluoroalkyl of 6 to 14 carbon atoms, E is ethylene, —[$M_1$]— is $$-[CH_2CH]-$$
$$|$$
$$CONH_2$$

x is 3 to 50 and y is 0

The structures of the fluorinated synergists (Component F) may be chosen from compounds represented by the formula $$R_f\text{-}T_m\text{-}Z$$

as described and defined in U.S. Pat. No. 4,090,167 incorporated herein by reference. Illustrative examples of $R_f$-synergists which can be used in the compositions of this invention also include
$R_f SO_2NH_2$,
$R_f SO_2N(CH_2CH_2OH)_2$,
$R_f SO_2N(C_2H_5)CH_2CHOHCH_2OH$,
$R_f CH_2CH_2SCH_2CH_2CONH_2$,
$R_f CH_2OH$,
$R_f CH_2CHOHCH_2OH$, and
$R_f CHOHCH_2OH$, where $R_f$ is perfluoroalkyl of 4 to 12 carbon atoms.

The hydrocarbon surfactant component G is broadly chosen from ionic, amphoteric and nonionic surfactants as described in U.S. Pat. No. 4,090,967.

Suitable hydrocarbon anionic surfactants include $C_8$–$C_{14}$-alkyl carboxylic acids and salts thereof, $C_8$–$C_{14}$-alkyl hydrogen sulfates and the corresponding sulfonic acids and salts thereof. $C_8$–$C_{14}$-alkyl ethoxy sulfates and salts thereof, alpha olefin sulfonates of 6 to 14 carbon atoms, $C_8$–$C_{14}$-alkyl amido alkylene sulfonates, and the like. Preferred are carboxylic or sulfonic acids as they are hydrolytically stable.

Suitable amphoteric hydrocarbon surfactants are those which contain in the same molecule, amino and carboxy, sulfonic acid, sulfuric ester or the like. Higher alkyl ($C_6$–$C_{14}$) betaines and sulfobetaines are included. Most preferred amphoteric hydrocarbon surfactants are the $C_6$–$C_{16}$-alkyl amino $C_2$–$C_4$-alkylene carboxylic acids, the corresponding $C_6$–$C_{16}$-alkylamino di-$C_2$–$C_4$-alkylene carboxylic acids and their salts, such as $C_{12\text{-}14}H_{25\text{-}29}NHCH_2CH_2COOH$ (Deriphat 170C) and $$C_{12}H_{25}N \begin{array}{c} CH_2CH_2COOH \\ \\ CH_2CH_2COONa \end{array}$$
(Deriphat 160C)

The hydrocarbon nonionic surfactant, in addition to acting as an interfacial tension depressant can serve as a stabilizer and solubilizer for the AFFF compositions, particularly when they are diluted with hard water or sea water. In addition, they serve to control foam drainage, foam viscosity and foam expansion. Suitable nonionic surfactants include polyethoxylated (5 to 40 units) derivatives of: alkyl phenols, linear or branched chain $C_6$–$C_{16}$ alcohols, $C_6$–$C_{16}$ alkyl mercaptans, $C_6$–$C_{16}$ alkanoic acids, $C_6$–$C_{16}$ alkyl amines or amides, or polyethoxylated propylene oxides.

The solvent component (H) are alcohols or ethers as described in U.S. Pat. No. 4,090,967.

Preferred solvents are 1-butoxyethoxy-2-propanol, diethyleneglycol monobutyl ether, hexylene glycol, or glycerol.

Component I is an electrolyte, typically a salt of a monovalent or polyvalent metal of Groups 1, 2 or 3, or organic base.

Preferred are polyvalent salts such as magnesium sulfate, magnesium nitrate or strontium nitrate.

High molecular weight foam stabilizers such as polyethyleneglycol, polyacrylamide, hydroxypropyl cellulose, or polyvinylpyrrolidone comprise component K.

Component L are polysaccharides from natural sources which may have been chemically modified. Preferred are heteropolysaccharides from bacterial fermentation which have been chemically modified.

The thixotropic polysaccharides are especially useful in compositions used to fight hydrophilic organic liquid fires. Such compositions, suitable for fighting both hydrophobic and hydrophilic organic liquid fires, are termed in the art as universal AFFF agents. Suitable thixotropic agents include those polysaccharides disclosed in U.S. Pat. No. 3,915,800 or 4,149,599.

Still other components which may be present in the formula are:

Buffers whose nature is essentially non-restricted and which are exemplified by Sorensen's phosphate or McIlvaine's citrate buffers.

Corrosion inhibitors whose nature is non-restricted so long as they are compatible with the other formulation ingredients.

Chelating agents whose nature is non-restricted, and which are exemplified by polyaminopolycarboxylic acid ethylenediaminetetraacetic acid, citric acid, tartaric acid, nitrilotriacetic acid hydroxyethylethylenediaminetriacetic acid and salts thereof. These are particularly useful if the composition is sensitive to water hardness.

Bacteriostats whose nature is unrestricted, but are necessary if polysaccharides are present. They may be exemplified by ortho phenylphenol.

The concentrates of this invention are effective fire fighting compositions over a wide range of pH, but generally such concentrates are adjusted to a pH of 6 to 9, and more preferably to a pH of 7 to 8.5, with a dilute acid or alkali. For such purpose may be employed organic or mineral acids such as acetic acid, oxalic acid, sulfuric acid, phosphoric acid and the like or metal hydroxides or amines such as sodium or potassium hydroxides, triethanolamine, tetramethylammonium hydroxide and the like.

As mentioned above, the compositions of this invention are concentrates which must be diluted with water before they are employed as fire fighting agents. Although at the present time the most practical, and therefore preferred, concentrations of said composition in water are 3% and 6% because of the availability of fire fighting equipment which can automatically admix the concentrate with water in such proportions, there is no reason why the concentrate could not be employed in lower concentrations of from 0.5% to 3% or in higher concentrations of from 6% to 12%. It is simply a matter of convenience, the nature of fire and the desired effectiveness in extinguishing the flames.

An aqueous AFFF concentrate composition which would be very useful in a 6% proportioning system comprises D. 0.05 to 0.3% by weight of an $R_f \cdot R_f$ complex.
E. 0 to 30% by weight of fluorochemical surfactants.
F. 0.1 to 0.3% by weight of fluorochemical synergist.
G. 0.05 to 3% by weight of hydrocarbon surfactant.
H. 0 to 25% by weight of solvent.
I. 0 to 2% by weight of electrolyte.
K. 0 to 2% by weight of foam stabilizer.
L. 0 to 5% by weight of polysaccharide.
M. Water in the amount to make up the balance of 100%.

Each component D to M may consist of a specific compound or mixtures o compounds.

The subject composition can be also readily dispensed from an aerosol type container by employing a conventional inert propellant such as Freon 11, 12, $N_2$ or air. Expansion volumes as high as 50 based on the ratio of air to liquid are attainable.

The major element of the AFFF system of this invention is the presence of the instant $R_f \cdot R_f$ complexes.

The above compositions are concentrates which, as noted above, when diluted with water, form very effective fire fighting formulations by forming a foam which deposits a tough film over the surface of the flammable liquid which prevents its further vaporization and thus extinguishes the fire.

It is a preferred fire extinguishing agent for flammable solvent fires, particularly for hydrocarbons and polar solvents of low water solubility, in particular for:

Hydrocarbon Fuels—such as gasoline, heptane, toluene, hexane, Avgas, VMP naphtha, cyclohexane, turpentine and benzene;

Polar Solvents of Low Water Solubility—such as butyl acetate, methyl isobutyl ketone, butanol, ethyl acetate, and Polar Solvents of High Water Solubility—such as methanol, acetone, isopropanol, methyl ethyl ketone, ethyl cellosolve and the like.

It may be used concomitantly or successively with flame suppressing dry chemical powders such as sodium or potassium bicarbonate, ammonium dihydrogen phosphate, $CO_2$ gas under pressure, or Purple K, as in so-called Twin-agent systems. A dry chemical to AFFF agent ratio would be from 10 to 30 lbs. of dry chemical to 2 to 10 gallons AFFF agent at use concentration (i.e. after 0.5%, 1%, 3%, 6% or 12% proportioning). In a typical example 20 lbs. of a dry chemical and 5 gals. of AFFF agent could be used. The composition of this invention could also be used in conjunction with hydrolyzed protein or fluoroprotein foams.

The foams of the instant invention do not disintegrate or otherwise adversely react with a dry powder such as Purple-K Powder (P-K-P). Purple-K Powder is a term used to designate a potassium bicarbonate fire extinguishing agent which is free-flowing and easily sprayed as a powder cloud on flammable liquid and other fires.

The concentrate is normally diluted with water by using a proportioning system such as, for example, a 3% or 6% proportioning system whereby 3 parts or 6 parts of the concentrate is admixed with 97 or 94 parts, respectively, of water. This highly diluted aqueous composition is then used to extinguish and secure the fire.

Today's commercial AFFF agents are only capable for use on 6, 3 and 1% proportioning systems. The compositions of the instant AFFF agents and the ranges of the amounts of the different active ingredients in these novel AFFF agents can be expressed for 0.5 to 12% proportioning systems. If the concentration in a composition for 6% proportioning is doubled then such a concentrate can be used for a 3% proportioning system. Similarly, if the concentration of such a 6% proportioning system is increased by a factor of 6 then it can be used as a 1% proportioning system.

EXPERIMENTAL PART

The following examples are illustrative of various representative embodiments of the invention, and are not to be interpreted as limiting the scope of the appended claims. In the examples, all parts are by weight unless otherwise specified.

Examples 1 through 10 illustrate the synthesis of the novel $R_fR_f$ ion-pair complexes as well as their efficiency as surface tension depressants in comparison with their precursor anionic and cationic fluorochemical surfactants (Tables 2 through 5).

Example 11 demonstrates the utility of the novel $R_fR_f$ ion-pair complexes as oil and water repellent finishes for paper and textiles.

Tables 6 through 12 list the key components used for the formulation of preferred $R_fR_f$ ion-pair complex-based AFFF agents, namely (a) selected $R_fR_f$ ion-pair complexes (Table 6), (b) selected fluorochemical surfactants (Table 7), (c) selected fluorochemical synergists (Table 8), (d) selected hydrocarbon surfactants (Table 9), (e) selected solvents (Table 10), (f) selected electrolytes (Table 11) and (g) selected foam stabilizers (Table 12).

Examples 12 through 27 show selected AFFF compositions derived from key components as listed in Tables 6 through 12, as well as comparative performance data obtained with and without $R_fR_f$ ion-pair complexes present in the AFFF agent compositions.

In the examples, references are made to specifications used by the industry and primarily the military and to proprietary tests to evaluate the efficiency of selected compositions. More specifically, the examples refer to the following specifications and laboratory test method:

1. Surface Tension and Interfacial Tension—ASTM D-1331-56

2. Laboratory Sealability Test

Objective: To measure the ability of a fluorochemical AFFF formulation (at the end use concentration) to form a film across, and seal a cyclohexane surface.

Procedure: Ten mls of cyclohexane is pipetted into a 48 mm evaporating dish in the evaporometer cell. Helium flowing at 1000 cc per minute flushes the cyclohexane vapors from the cell through a 3 cm IR gas cell mounted on a PE 257 infrared spectrophotometer (a recording infrared spectrophotometer with time drive capability). The IR absorbance of the gas stream in the region of 2850 cm$^{-1}$ is continuously monitored as solutions of formulations are infused onto the surface. Formulations are infused onto the cyclohexane surface at a rate of 0.17 ml per minute using a syringe pump driven 1 cc tuberculin syringe fitted with a 13 cm 22 gauge needle, whose needle is just touching the cyclohexane surface.

Once the absorbance for "unsealed" cyclohexane is established, the syringe pump is started. Time zero is when the very first drop of formulation solution hits the surface. The time of 50% seal, percent seal at 30 seconds and 1-4 minutes are recorded. Time to 50% seal relates well to film speed (see below), percent seal in 30 seconds and 1-4 minutes relate well to the efficiency and effectiveness of the film as a vapor barrier (film persistence).

3. Field Fire Tests As Defined in MIL-24385B for Aqueous Film Forming Foam

The most critical test of the subject compositions is actual fire tests. The detailed procedures for such tests on 28, 50 square foot fires are set forth in the U.S. Navy Specification MIL-F-24385B.

Procedure: Premixes of the compositions of this invention are prepared from 0.5 to 12% proportioning concentrates with tap or sea water, or the AFFF agent is proportioned by means of an in-line proportioning educator system. The test formulation in any event is applied at an appropriate use concentration.

The efficacy of the compositions of the present invention to extinguish hydrocarbon fires was proven repeatedly and reproducibly on 28-square foot (2.60 sq. m) and on 50-square feet (4.65 sq. meter) gasoline fires. The fire performance tests and subsidiary tests—foamability, film formation, sealability, film speed, viscosity, drainage time, spreading coefficient, and stability, all confirmed that the compositions of this invention performed better than prior art AFFF compositions.

The most important criteria in determining the effectiveness of a fire fighting composition are:

1. Control Time—The time to bring the fire under control or secure it after a fire fighting agent has been applied.

2. Extinguishing Time—The time from the initial application to the point when the fire is completely extinguished.

3. Burn-Back Time—The time from the point when the flame has been completely extinguished to the time when the hydrocarbon liquid substantially reignites when the surface is subjected to an open flame.

4. Summation of % Fire Extinguished—When 50 square foot (4.645 sq. m.) fires are extinguished the total of the "percent of fire extinguished" values are recorded at 10, 20, 30 and 40 second intervals. Present specification for 50 square foot fires require the "Summation" to fires be 300 or greater.

28-Square-Foot Fire Test

This test was conducted in a level circular pan 6 feet (1.83 m) in diameter (28 square feet—2.60 square maters), fabricated from ¼" (0.635 cm) thick steel and having sides 5" (12.70 cm) high, resulting in a freeboard of approximately 2½" (6.35 cm) during tests. The pan was without leaks so as to contain gasoline on a substrate of water. The water depth was held to a minimum, and used only to ensure complete coverage of the pan with fuel. The nozzle used for applying agent had a flow rate of 2.0 gallons per (g.p.m.) (7.57 1 per minute) at 100 pounds per square inch (p.s.i.) (7.03 kg/sq. cm) pressure. The outlet was modified by a "wing-tip" spreader having a ⅛" (3,175 mm) wide circular arc orifice 1⅞" (7.76 cm) long.

The premix solution in fresh water or sea water was at 70°+−10° F. (21° C.+−5.5° C.). The extinguishing agent consisted of a 6-percent proportioning concentrate or its equivalent in fresh water or sea water and the fuel charge was 10 gallons (37.85 1) of gasoline. The complete fuel charge was dumped into the diked area within a 60-second time period and the fuel was ignited within 60 seconds after completion of fueling and permitted to burn freely for 15 seconds before the application of the extinguishing agent. The fire was extinguished as rapidly as possible by maintaining the nozzle 3½ to 4 feet above the ground and angled upward at a distance that permitted the closest edge of the foam pattern to fall on the nearest edge of the fire. When the fire was extinguished, the time-for-extinguishment was recorded continuing distribution of the agent over the test area until exactly 3 gallons (11.36 1) of premix has been applied (90-second application time).

The burnback test was started within 30 seconds after the 90-second solution application. A weighted 1-foot (30.48 cm) diameter pan having 2" (5.08 cm) side walls and charged with 1 quart (0.046 1) of gasoline was placed in the center of the area. The fuel in the pan was ignited just prior to placement. Burnback time commenced at the time of this placement and terminated when 25 percent of the fuel area (7 square feet—0.65 sq. meter), (36-inch diameter—232.26 sq. cm), originally covered with foam was aflame. After the large test pan area sustained burning, the small pan was removed.

EXAMPLE 1

3-(1,1,2,2-tetrahydroperfluorooctylthio)-2-hydroxypropyltrimethylammonium 2-methyl-2-(3-[1,1,2,2-tetrahydroperfluorooctylthio]-propanesulfonate $C_6F_{13}CH_2CH_2SCH_2CH_2CONHC(CH_3)_2CH_2SO_3^\ominus.N^\oplus(CH_3)_3CH_2CHOHCH_2SCH_2CH_2C_6F_{13}$ Sodium 2-methyl-2-(3-[1,1,2,2-tetrahydroperfluorooctylthio]-propionamide)-1-propanesulfonate (42.0 gms, 30% actives, 0.02 moles, and 3-(1,1,2,2-tetrahydroperfluorooctylthio)-2-hydroxypropyltrimethylammonium chloride (39.0 gms, 28.7% actives, 0.02 moles) were combined and dialyzed for 48 hours in distilled water in a commercially available seamless dialysis tubes made from regnerated cellulose, 64 mm flat width.

The product was obtained by evaporating the contents of the dialysis bag in a draft oven at 60° C. The product was washed with several liters of distilled water, re-evaporated and then thoroughly dried under high vacuum. It was obtained in essentially quantitative yield and slowly crystallized to a m.p. 74°–98°.

Analysis for $C_{29}H_{36}F_{26}N_2O_5S_3$: Calc.: C, 32.16; H, 3.35; F, 45.61; N, 2.59. Found: C, 31.96; H, 3.22; F, 45.26; N, 2.48.

In the following examples, the specified $R_f$-anionic and $R_f$-cationic surfactants were combined and dialyzed in a similar fashion to Example 1. The products were all obtained in near quantitative yield.

EXAMPLE 2

Sodium 2-methyl-2-(3-[1,1,2,2-tetrahydroperfluorooctylthio]-propionamido)-1-propanesulfonate (1.22 gms, 2 millimoles) was combined in the manner of Example 1, with N-1,1,2,2-tetrahydroperfluorodecyl pyridinium iodide. The product is a white solid having a m.p. of 112°–113.5° C., of the structure

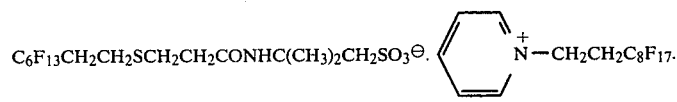

Analysis for $C_{30}H_{26}F_{30}N_2O_4S_2$: Calculated: C, 32.39; H, 2.36; F, 51.23; N, 2.52; S, 5.76. Found: C, 32.45; H, 2.41; F, 51.18; N, 2.51; S, 6.15.

EXAMPLE 3

Sodium 2-methyl-2-(3-[1,1,2,2-tetrahydroperfluorooctylthio]-propionamide)-1-propanesulfonate (0.61 gm, 1 millimole) was reacted, in the manner according to Example 1, with N-1,1,2,2-tetrahydroperfluorooctyl pyridinium iodide (0.55 gms, 1 millimole).

The product is an off-white solid having an m.p. of 88.0°–90.5° C. The product is of the structure

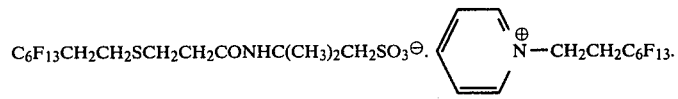

Analysis for $C_{28}H_{26}F_{26}N_2O_4S_2$: Calculated: C, 33.21; H, 2.59; F, 48.78; N, 2.77; S, 6.33. Found: C, 33.23; H, 2.38; F, 48.05; N, 2.75; S, 6.64.

EXAMPLE 4

Sodium 2-methyl-2-(3-[1,1,2,2-tetrahydroperfluorooctylthio]propionamido)-1-propanesulfonate (1.22 gms, 2 millimoles) was reacted, in the manner according to Example 1, with N-[perfluorooctylsulfonamido)propyl]-N,N,N-trimethylammonium iodide (1.45 gms, 2 millimoles). The product is a tan solid having an m.p. of 133°–140° C. The product has the structure

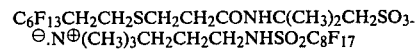

Analysis for $C_{29}H_{33}F_{30}N_3O_6S_3$: Calculated: C, 29.38; H, 2.81; F, 48.07; N, 3.54; S, 8.11. Found: C, 29.47; H, 2.85; F, 47.86; N, 3.50; S, 8.29.

EXAMPLE 5

Sodium 2-methyl-2-(3-[1,1,2,2-tetrahydroperfluoroalkylthio]propionamido)-1-propanesulfonate wherein perfluoroalkyl has an $R_f$ distribution of 49% $C_6$, 49% $C_8$ and 2% $C_{10}$, was reacted, according to the manner of Example 1, with an equimolar amount of N-(3-[1,1,2,2-tetrahydroperfluoroalkylthio]-2-hydroxypropyl)-N,N,N-trimethyl ammonium chloride wherein the perfluoroalkyl has an $R_f$ distribution of 49% $C_6$, 49% $C_8$ and 2% $C_{10}$. The product is a white solid which softens at 85° C. and has an m.p. of 148°–155° C. The product has the structure

EXAMPLE 6

The products of Examples 1, 2 and 4 were tested for their respective solubility in distilled water. The $R_f\cdot R_f$ complexes exhibit the following solubility in weight %:
Example 1: $5 \times 10^{-3}$
Example 2: $1.2 \times 10^{-3}$
Example 4: $1 \times 10^{-3}$
None of the $R_f\cdot R_f$ complexes of Examples 1, 2 and 4 exhibited micellar behavior. The concentrated solutions of Example 1 and 2 exhibit a surface tension of 16.9 and 17.5 dynes/cm, respectively.

EXAMPLE 7

Anionic and cationic fluorochemical surfactants as listed in Table 2a were reacted in various molar ratios as shown in Table 2b. The surface tensions measured at 0.1% and 0.01% total actives as listed in Table 2b indicate, that the results obtained with equimolar mixtures of the anionic and cationic surfactants (quantitative yield of $R_fR_f$ ion pair complex) provide the lowest surface tension. Similarly it is shown in Table 3, that the $R_fR_f$ ion pair complexes are superior surface tension depressants as compared with the precursor anionic and cationic surfactants. Data in Table 3 also indicate that fluorochemical surfactants with selected $R_f$-chains or homolog distributions have preferred properties. The combination A2/C2 in Table 3 exhibits the lowest surface tensions ever reported at such a low concentration of a fluorochemical surface tension sepressant (26.9 dynes/cm at 0.001% by weight of the $R_fR_f$ ion-pair complex).

TABLE 2a

| $R_f$ Surfactant | Name | Formula/$R_f$ Composition | | | |
|---|---|---|---|---|---|
| Fluorinated Anionic Surfactants | | | | | |
| | | $R_fCH_2CH_2SCH_2CH_2CONHC(CH_3)_2CH_2SO_3Na$ wherein: | | | |
| | | % $C_6F_{13}$ | % $C_8F_{17}$ | % $C_{10}F_{21}$ | % $C_{12}F_{26}$ |
| A1 | 2-Methyl-2-(3-1,1,2,2,-tetrahydro-perfluoroalkylthio propionamide)-1-propanesulfonic acid, sodium salt | 33 | 36 | 22 | 6 |
| A2 | as above | 44 | 49 | 1 | |
| A3 | as above, 45% | 100 | | | |
| Fluorinated Cationic Surfactants | | | | | |
| | | $R_fCH_2CH_2SCH_2CHOHCH_2\overset{+}{N}(CH_3)Cl^-$ wherein: | | | |
| | | % $C_6F_{13}$ | % $C_8F_{17}$ | % $C_{10}F_{21}$ | % $C_{12}F_{26}$ |
| C1 | 3-(1,1,2,2-tetrahydroperfluoro-alkylthio)-2-hydroxypropyl-trimethylammonium chloride | 33 | 36 | 22 | |
| C2 | as above | 49 | 49 | 1 | |
| C3 | as above, 45% | 100 | | | |

TABLE 2b

Surface Tension Effect of Varied Mole Ratios of Anionic and Cationic Fluorochemical Surfactants

| | Mol. % Anionic Fluorochemical Surfactant A1 | Mol. % Cationic Fluorochemical Surfactant C1 | Surface Tension |
|---|---|---|---|
| 0.1% Total Actives | 100 | 0 | 27.1 |
| | 75 | 25 | 21.9 |
| | 50 | 50 | 16.9 |
| | 25 | 75 | 18.7 |
| | 0 | 100 | 21.6 |
| 0.01% Total Actives | 100 | 0 | 29.1 |
| | 75 | 25 | 23.5 |
| | 50 | 50 | 17.6 |
| | 25 | 75 | 22.3 |
| | 0 | 100 | 31.0 |

TABLE 3

Surface Tension Data at Various Concentrations of Anionic and Cationic Fluorochemical Surfactants and Their $R_fR_f$ Complexes

| Fluorochemical | 1.0% | 0.1% | 0.01% | 0.001% | 0.0001% |
|---|---|---|---|---|---|
| A1 | 26.0 | 27.1 | 29.1 | 40.1 | |
| A2 | 25.6 | 24.5 | 24.4 | 41.7 | 69.8 |
| C1 | 19.5 | 21.6 | 28.1 | 49.6 | 67.4 |
| C2 | 20.5 | 20.0 | 29.6 | 52.3 | 66.6 |
| A1/C1 | | | 17.4$^a$ | 55.1 | |
| A2/C2 | | 16.1 | 16.1 | 26.9 | 56.6 |

$^a$ppt (24.3 at 0.005%)

Analogous results are obtained when the salt of A3 and C1, C2 and C3 are prepared, as well as those of A1 and A2 with C3.

EXAMPLE 8

In the following equimolar amounts of A3 as specified in Example 7 is reacted according to the procedure as set forth in Example 1 with each of C4, C5, C6, C7, C8, C9, C10 and C11.

$$C_8F_{17}SO_2NHC_3H_6\overset{\oplus}{N}(CH_3)_3\overset{\ominus}{Cl} \qquad C4$$

$$C_8F_{17}SO_2NHC_3H_6\overset{\oplus}{N}(CH_3)_2C_2H_5\overset{\ominus}{O}SO_2OC_2H_5 \qquad C5$$

$$C_8F_{17}SO_2NHC_3H_6\overset{\oplus}{N}(CH_3)_3\overset{\ominus}{I} \qquad C6$$

$$C_7F_{15}CONHC_3H_6\overset{\oplus}{N}(CH_3)_3\overset{\ominus}{Cl} \qquad C7$$

$$C_8F_{17}SO_2NHC_3H_6\overset{\oplus}{N}(CH_3)_2CH_2C_6H_5\overset{\ominus}{Cl} \qquad C8$$

$$C_8F_{17}SO_2N(CH_3)C_3H_6\overset{\oplus}{N}(CH_3)_3\overset{\ominus}{I} \qquad C9$$

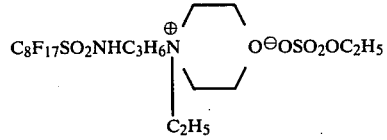

C10

$$C_6F_{13}CH_2CH_2SCH_2CH_2\overset{\oplus}{N}(CH_3)_3\overset{\ominus}{I} \qquad C11$$

The resulting $R_f$-$R_f$ complexes, in each case, exhibit the desirable aqueous surface tension reduction characteristics at low concentrations.

EXAMPLE 9

$R_fR_f$ ion-pair complexes were synthesized from commercial anionic and cationic fluorochemical surfactants as listed in Table 4. Surface tension comparisons of the precursor fluorochemical surfactants at 0.01% by weight in water versus the $R_fR_f$ ion pair complexes at 0.01% by weight in water show, that the $R_fR_f$ ion pair complexes provide generally lower surface tension than the precursor fluorochemical surfactants.

TABLE 4

Surface Tension Values of Various Cationic/Anionic Ion Pair Complexes

| Cationic Surfactant Alone at 0.01% | Cationic/Anionic Ion Pair Complex at 0.01% | Anionic Surfactant Alone at 0.01% |
|---|---|---|
| LODYNE S-106 28.1 | 16.8 | LODYNE S-102 29.0 |
| LODYNE S-106 28.1 | 16.3 | LODYNE S-112 20.2 |
| LODYNE S-106 28.1 | 18.6 | FC 95 42.2 |
| LODYNE S-106 28.1 | 17.9 | FC 128 24.7 |
| LODYNE S-106 28.1 | 19.6 | Zonyl FSE 23.5 |
| LODYNE S-106 28.1 | 23.9 | Zonyl FSJ 24.9 |
| LODYNE S-106 28.1 | 24.9 | Monflor 31 29.5 |
| Zonyl FSC 27.5 | 16.5 | LODYNE S-102 29.0 |
| Zonyl FSC 27.5 | 16.5 | FC 128 24.7 |
| Zonyl FSC 27.5 | 24.3 | Zonyl FSJ 24.9 |
| Zonyl FSC 27.5 | 22.3 | Monflor 31 29.5 |
| Monflor 71 47.1 | 25.6 | Monflor 31 29.5 |
| LODYNE S-116 20.3 | 16.1 | LODYNE S-102 29.0 |
| LODYNE S-116 20.3 | 16.5 | LODYNE S-112 20.2 |
| FC-134 17.8 | 17.2 | LODYNE S-102 29.0 |
| FC-134 17.8 | 16.7 | FC 128 24.7 |

TABLE 5

Surface Tension Values of $R_fR_f$ Ion-Pair Complexes at Various Concentrations

| Cationic Surfactant | | $R_fR_f$ Ion Pair | | Anionic Surfactant | | |
|---|---|---|---|---|---|---|
| 0.001% | 0.01% | 0.0005% | .001% | 0.0055% | 0.01% | |
| Cl 49.6 | 28.1 | 28.7 | — | — | 42.2 | FC-95 |
| | | 21.8 | — | — | 24.7 | FC-128 |
| | | 27.3 | — | 29.0 | 21.2 | Zonyl FSP |
| | | 25.3 | 40.1 | 28.1 | 29.1 | Al |

EXAMPLE 10

Table 5 shows the high efficiency of $R_fR_f$ ion pair complexes as surface tension depressants as a function of concentration in water. It also shows the high effectiveness of the complexes as measured by the minimum value to which it can lower the surface tension. The efficiency and effectiveness of the subject cationic anionic complexes both are appreciably better than the commercial precursor fluorochemical surfactants.

EXAMPLE 11

The $R_f$-cationic/$R_f$-anionic ion pair complexes demonstrate oil repellency when applied as a paper size or as a textile finish.

Paper Size—Dry paper pulp is diluted with water and to this suspension are added a dilute solution of the $R_fR_f$ complex prepared from A1 and C1. Adjuvants are added and the slurry is then cast as a paper mat. After drying, this sheet gives a 3M oil repellency kit rating of 4 at 0.06% fluorine on weight of paper [Kit No. 4=70 parts castor oil/15 parts toluene/15 parts heptane].

Textile Finish—A solution of the $R_f \cdot R_f$ complex prepared from A1 and C1 was applied in a pad bath to 65/35 polyester cotton twill. At a concentration of 0.06% F on the dry fabric in the presence of a permanent press finish, the swatch gave an AATCC oil repellency rating of 3.

TABLE 6

$R_fR_f$ Complexes

Formula: $R_fCH_2CH_2SCH_2CONHC(CH_3)_2CH_2SO_3^{\ominus} \cdot N^{\oplus}(CH_3)_3CHOHCH_2SCH_2CH_2R_f$ wherein;

| $R_fR_f$ Complexes | Name | Anionic Segment | | Cationic Segment | |
|---|---|---|---|---|---|
| | | % $C_6F_{13}$ | % $C_8F_{17}$ | % $C_6F_{13}$ | % $C_8F_{17}$ |
| D1 | 3-(1,1,2,2-tetrahydroperfluoroalkylthio)-2-hydroxy propyltrimethylammonium 2-methyl-2-(3[1,1,2,2-tetrahydroperfluoroalkylthio]propionamide)-1-propane sulfonate | 50 | 50 | 20 | 80 |
| D2 | As above | 50 | 50 | 95 | — |
| D3 | As above | 95 | — | 95 | — |
| D4 | As above | 20 | 80 | 20 | 80 |
| D5 | As above | 95 | — | 20 | 80 |
| D6 | As above | 20 | 80 | 95 | — |
| D7 | As above | 95 | — | 50 | 50 |
| D8 | As above | 20 | 80 | 50 | 50 |

TABLE 7

Fluorinated Surfactants

Formula: $R_fCH_2CH_2SCH_2CH_2CONHC(CH_3)_2CH_2SO_3Na$ wherein;

| $R_f$ Surfactant | Name | % $C_6F_{13}$ | % $C_8F_{17}$ | % $C_{10}F_{21}$ |
|---|---|---|---|---|
| E1 | 2-Methyl-2-(3-[1,1,2,2-tetrahydroperfluoroalkylthio]propanamide)-2-propanesulfonic acid; sodium salt | 40 | 42 | 12 |
| E2 | As above | 50 | 50 | — |
| E3 | As above | 95 | — | — |
| E4 | As above | 20 | 80 | — |
| E5 | As above | 33 | 36 | 23 |
| E6 | As above | — | 11 | 60 |
| E7 | Perfluoroalkylthio oligomer | (as in copending application Ser. No. 129,872 filed 3/13/80) | | |

TABLE 8

$R_f$ Synergists

| $R_f$ Synergist | Name | Formula |  |  |
|---|---|---|---|---|
|  |  | $R_fCH_2CH_2SCH_2CH_2CONH_2$ wherein: |  |  |
|  |  | % $C_6F_{13}$ | % $C_8F_{17}$ | % $C_{10}F_{21}$ |
| F1 | 3-[1,1,2,2-tetrahydro-perfluoroalkylthio-] propionamide | 74 | 17 | 2 |
| F2 | As above | 95 | 2 | — |
| F3 | As above | 35 | 36 | 20 |

TABLE 9

Hydrocarbon Surfactants

| Hydrocarbon Surfactants | Name % Actives as Noted or ~100% | Formula of Commercial Name |
|---|---|---|
| G1 | Partial sodium salt of N—alkyl β-iminodipropionic acid, 30% | wherein: R— $C_{12}H_{25}$(Deriphat 160C, General Mills) |
| G2 | Sodium alkyl sulfate | A 50/50 mixture of $C_8H_{17}$ and $C_{10}H_{21}$ |
| G3 | Disodium salt of N—alkyl-N,N—bis(2-propionamide-2-methyl-1-propane sulfonate | $RN[CH_2CH_2CONHC(CH_3)_2CH_2SO_3Na]_2$ wherein: R is $C_8H_{17}$ |
| G4 | As above | As above wherein R = $C_6H_{13}OCH_2CH_2CH_2$— |
| G5 | Octylphenoxypolyethoxyethanol (12) 99% | Triton X-102, Rohm & Haas |
| G6 | Polyoxyethylene (23) lauryl ether | Brij 35, I.C.I. |

TABLE 10

Solvents

| Solvents | Name |
|---|---|
| H1 | 1-butoxyethoxy-2-propanol |
| H2 | 2-methyl-2,4-pentanediol |
| H3 | Ethylene glycol |
| H4 | Diethylene glycol monobutyl ether |
| H5 | Glycerine |
| H6 | Propylene glycol |

TABLE 11

Electrolytes

| Electrolyte | Name |
|---|---|
| I1 | magnesium sulfate |
| I2 | magnesium nitrate |
| I3 | strontium nitrate |

TABLE 12

Foam Stabilizers

| Foam Stabilizers | Name |
|---|---|
| K1 | polyethylene glycol |
| K2 | hydroxypropyl cellulose |
| K3 | polyvinyl pyrrolidone |

EXAMPLES 12 AND 13

A comparison was made between AFFF compositions with regard to laboratory performance. As noted below the formulation with the $R_f:R_f$ complex was appreciably faster at normal use dilution and had a significantly lower surface tension even under high dilution.

TABLE 13

| AFFF Component | No. | % |
|---|---|---|
| $R_f:R_f$ complex | D2 | Variable |
| $R_f$ surfactant | E2 | 0.75 |
| $R_f$ synergist | F2 | 0.1 |
| $R_h$ surfactant | G1 + G3 + G5 | 0.75 + 1.01 + 0.60 |
| Solvent | H4 + H6 | 14.0 + 8.0 |
| $MgSO_4$ | I1 | 0.24 |
| Water |  | Balance |
| Example Number |  | 12 | 13 |
| $R_f:R_f$ complex, % |  | None | 0.006 |
| Laboratory Performance |  |  |  |
| Seal Speed (6% tap), sec |  | 12 | 12 |
| Seal Speed (6% sea), sec |  | 24 | 20 |
| Seal Speed (3% tap), sec |  | 25 | 32 |
| Seal Speed (3% sea), sec |  | 50 | 56 |
| Surface tension (3% distilled), dynes/cm |  | 20.7 | 18.1 |
| Spreading coefficient (3% distilled), dynes/cm |  | 2.1 | 4.7 |

EXAMPLES 14–17

Particularly well performing AFFF agents can be made by the judicious choice of $R_f:R_f$ complex and $R_h$ surfactants

TABLE 14

| AFFF Component | No. | % | % | % | % |
|---|---|---|---|---|---|
| $R_f:R_f$ complex | D2 | .06 | 0.31 | 0.23 | None |
| $R_f$ surfactant | E2 + E7 | 1.12 + 0.4 | 0.88, — | 1.08, — | 0.90, — |
| $R_f$ synergist | F2 | 0.19 | 0.18 | 0.20 | 0.15 |
| $R_h$ surfactant | G1 + G3 + G5 | 0.75 + 1.01 + 0.60 | 0.75 + 1.01 + 0.60 | 0.75 + 1.01 + 0.60 | 0.75 + 1.01 + 0.60 |
| Solvent | H4 + H6 | 14.0 + 8.0 | 14.0 + 8.0 | 14.0 + 6.0 | 9.0 + 8.0 |
| $MgSO_4$ | I1 | 0.24 | 0.24 | 0.24 | 0.24 |

TABLE 14-continued

| Water | Balance | Balance | Balance | Balance |
|---|---|---|---|---|
| Example Number | 14 | 15 | 16 | 17 |
| Control Time, sec. | 18 | 21 | 18 | 19 |
| Extinguishing Time, sec. | 41 | 35 | 36.5 | 42 |
| 40 Second Summation | 341 | 336 | 350 | 323 |
| Burnback Time, min. | 460 | 411 | 405 | 370 |
| Foam Expansion | 8.5 | 7.7 | 8.3 | 8.2 |
| 25% Drain Time, min. | 300 | 301 | 286 | 251 |

EXAMPLES 18–19

AFFF concentrates containing polysaccharide were tested for performance on non-polar and polar (methanol) fires. The performance was quite satisfactory in both regards.

TABLE 15

| AFFF Components | No. | % | |
|---|---|---|---|
| $R_f R_f$ complex | D2 | 0.06 | |
| $R_f$ surfactant | E2 | 0.72 | |
| $R_f$ synergist | F2 | 0.12 | |
| $R_h$ surfactant | G1 + G3 + G5 | 0.75 + 1.01 + 0.60 | |
| Solvent | H4 + H6 | Variable | |
| MgSO4 | I1 | 0.24 | |
| Polysaccharide | | Variable | |
| Water | | Balance | |
| Example Number | | 18 | 19 |
| Polysaccharide K8A13, % | | 1.5 | None |
| Solvent F4 + F6, % | | 10.0, None | 14.0 + 8.0 |
| FIRE TESTS: 28 ft² | | 6T* on Gasoline | 10T* on Methanol |
| Control Time, sec | | — | 39 |
| Extinguishing Time, sec | | 23 | 62 |
| Burnback Time, min | | 12.8 | 22.8 |
| Foam Expansion | | 6.9 | 7.4 |
| 25% Drain Time, min | | 25.3 | 53.5 |

*6T indicates tap water containing 6% of AFFF concentrate 10T indicates tap water containing 10% of AFFF concentrate

EXAMPLES 20–21

Large scale fire tests on 50 ft² fires were run on compositions differing only with regard to the presence of an $R_f R_f$ complex. As noted, the formulations with the complex had a more rapid fire knockdown as well as improved burnback performance and expansion.

TABLE 16

| AFFF Components | No. | % |
|---|---|---|
| $R_f R_f$ complex | D2 | Variable |
| $R_f$ surfactant | E2 | 0.67 |
| $R_f$ synergist | F2 | 0.12 |
| $R_h$ surfactant | G1 + G3 + G5 | 0.75 + 1.01 + 0.60 |
| Solvent | H4 + H6 | 9.0 + 8.0 |
| Water | | Balance |
| Example Number | 20 | 21 |
| $R_f R_f$ complex, % | None | 0.08 |
| FIRE TEST: 50 ft², | | |
| Control Time, sec. | 25–30 | 20–24 |
| Extinguishing Time, sec. | 48–54 | 44–50 |
| Burnback Time, min. | 301–346 | 357–373 |
| Foam Expansion | 6.1 | 6.8 |
| Extinguishing Time - 40 sec. summation | 288–298 | 317–323 |

EXAMPLES 22–25

AFFF concentrates differing only with regard to the presence of an $R_f R_f$ complex were tested for fish toxicity. A considerable improvement was always found when the complex was present.

TABLE 17

| AFFF Component | Nr. | % | | |
|---|---|---|---|---|
| $R_f R_f$ complex | D2 | Variable | | |
| $R_f$ surfactant | E2 | Variable | | |
| $R_f$ synergist | F2 | 0.13 | | |
| $R_h$ surfactant | G1-2 + G3 + G5 | Variable + 1.01 + 0.60 | | |
| Solvent | H4 + H6 | 14.0 + 8.0 | | |
| MgSO4 | I1 | 0.24 | | |
| Water | | Balance | | |
| Example Number | 22 | 23 | 24 | 25 |
| $R_f R_f$ complex, % | None | 0.23 | None | 0.35 |
| $R_f$ surfactant, % | 0.75 | 0.63 | 0.75 | 0.63 |
| $R_h$ surfactant, % | 0.75 (G1) | 0.75 (G1) | 1.20 (G2) | 1.20 (G2) |
| FISH TOXICITY | | | | |
| LC50-96 hr. ppm | 2500–3000 | >3000 | 3000–4000 | >4000 |

EXAMPLES 26–27

In Examples 25 and 26 it is clearly shown that the $R_f R_f$ complex appreciably aids fish toxicity of AFFF compositions.

TABLE 18

| AFFF Components | No. | % |
|---|---|---|
| $R_f R_f$ complex | D2 | Variable |
| $R_f$ surfactant | E2 | Approx. 0.875 |
| $R_f$ synergist | F2 | 0.15 |
| $R_h$ surfactant | G1 + G3 + G5 | 0.75 + 1.01 + 0.60 |
| Solvent | H4 + H6 | 9.0 + 8.0 |
| MgSO4 | I1 | 0.24 |
| Water | | Balance |
| Example Number | 26 | 27 |
| $R_f R_f$ complex, % | 0.06 | None |
| FISH TOXICITY | | |
| LC50-96 hr, ppm | ~5000 | ~2500 |

I claim:

1. A hydrolytically stable ion pair complex of the formula $$R_f—A—Q^{\ominus}.N^{\oplus}(R_1)(R_2)(R_3)—A'—R_f'$$

wherein $R_f$ and $R_f'$ independently represent perfluoroalkyl of 4 to 12 carbon atoms;

A and A' independently represent

—$CH_2CH_2$—S—alkylene—G''—alkylene— where G'' is independently —$SO_2NH$—, —$CONH$— or $$-\overset{OH}{\underset{|}{CH}}-,$$

and each alkylene is straight or branched chain alkylene of 1 to 6 carbon atoms;

$R_1$, $R_2$ and $R_3$ are independently hydrogen, phenyl, alkyl of 1 to 8 carbon atoms which is unsubstituted or is substituted by halo, hydroxy or phenyl; or is $-CHR_4CH_2O)_yR_5$ where y is 1 to 20, $R_4$ is hydrogen or alkyl of 1 to 4 carbon atoms and $R_5$ is hydrogen or methyl; or $R_1$ and $R_2$ taken together with the nitrogen to which they are attached represent piperidino, morpholino or piperazino; or $R_1$, $R_2$ and $R_3$ taken together with the nitrogen to which they are attached represent pyridinium or pyridinium substituted by alkyl of 1 to 4 carbon atoms; and Q represents the carboxy, sulfo, phosphato or phosphono anion.

2. An ion pair complex according to claim 1, wherein $R_1$, $R_2$ and $R_3$ are, methyl.

3. An ion pair complex according to claim 2, wherein Q is the sulfo, carboxy or phosphato anion.

4. An ion pair complex according to claim 2 of the formula $$R_f-CH_2CH_2SCH_2CH_2CONHC(CH_3)_2CH_2SO_3^{\ominus}\overset{\oplus}{N}(CH_3)_3CH_2\overset{OH}{\underset{|}{CH}}CH_2SCH_2CH_2R'_f$$

wherein $R_f$ and $R_f'$ independently represent perfluoroalkyl of 4 to 12 carbon atoms.

* * * * *